(12) United States Patent
Gonciarz et al.

(10) Patent No.: US 11,104,711 B2
(45) Date of Patent: Aug. 31, 2021

(54) GROWTH DIFFERENTIATION FACTOR 15 AGONIST COMPOUNDS AND METHODS OF USING THE SAME

(71) Applicant: Eli Lilly and Company, Indianapolis, IN (US)

(72) Inventors: Malgorzata Donata Gonciarz, Indianapolis, IN (US); Victor H. Obungu, Fishers, IN (US); Richard Todd Pickard, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 101 days.

(21) Appl. No.: 16/369,096

(22) Filed: Mar. 29, 2019

(65) Prior Publication Data
US 2019/0309033 A1 Oct. 10, 2019

Related U.S. Application Data

(60) Provisional application No. 62/653,759, filed on Apr. 6, 2018.

(51) Int. Cl.
| | | |
|---|---|---|
| *C07K 14/495* | (2006.01) | |
| *C07K 14/475* | (2006.01) | |
| *A61P 3/06* | (2006.01) | |
| *A61P 3/10* | (2006.01) | |
| *A61K 47/65* | (2017.01) | |
| *A61P 3/04* | (2006.01) | |
| *A61K 38/00* | (2006.01) | |
| *A61K 38/16* | (2006.01) | |
| *A61K 38/17* | (2006.01) | |
| *A61K 38/18* | (2006.01) | |
| *C07K 16/18* | (2006.01) | |
| *C07K 16/10* | (2006.01) | |

(52) U.S. Cl.
CPC ............ *C07K 14/495* (2013.01); *A61K 47/65* (2017.08); *A61P 3/04* (2018.01); *A61P 3/06* (2018.01); *A61P 3/10* (2018.01); *C07K 14/475* (2013.01); *C07K 16/1036* (2013.01); *C07K 16/18* (2013.01)

(58) Field of Classification Search
None
See application file for complete search history.

(56) References Cited

U.S. PATENT DOCUMENTS

| | | | | | |
|---|---|---|---|---|---|
| 5,288,931 | A | * | 2/1994 | Chang | ................. C07K 1/1133 435/69.1 |
| 7,112,660 | B1 | * | 9/2006 | Domingues | ........ C07K 14/5406 530/351 |
| 2003/0045474 | A1 | * | 3/2003 | Sailer | ..................... A61P 19/00 514/8.8 |
| 2013/0072420 | A1 | * | 3/2013 | Skerra | ..................... A61P 11/06 514/1.1 |
| 2014/0154743 | A1 | * | 6/2014 | Levy | ..................... C07K 16/00 435/69.6 |
| 2016/0120999 | A1 | * | 5/2016 | Shen | ....................... A61P 3/10 424/178.1 |

FOREIGN PATENT DOCUMENTS

| | | |
|---|---|---|
| WO | 2005113585 A2 | 12/2005 |
| WO | 2006031994 A2 | 3/2006 |
| WO | 2013113008 A1 | 8/2013 |
| WO | 2013148117 A1 | 10/2013 |
| WO | 2014120619 A2 | 8/2014 |
| WO | 2015017548 A2 | 2/2015 |
| WO | 2015017710 A1 | 2/2015 |
| WO | 2015197446 A1 | 12/2015 |
| WO | 2015198199 A1 | 12/2015 |
| WO | 2015200080 A1 | 12/2015 |
| WO | 2016018931 A1 | 2/2016 |
| WO | 2016069921 A1 | 5/2016 |
| WO | 2016069925 A1 | 5/2016 |
| WO | 2016131893 A1 | 8/2016 |
| WO | 2016161100 A1 | 10/2016 |
| WO | 2017109706 A1 | 6/2017 |
| WO | 2017121865 A1 | 7/2017 |
| WO | 2017147742 A1 | 9/2017 |
| WO | 2017152105 A1 | 9/2017 |
| WO | 2017196647 A1 | 11/2017 |

OTHER PUBLICATIONS

Tokuriki et al., 2009, Curr. Opin. Struc. Biol. 19:596-604.*
Fenton et al., 2020, Medicinal Chemistry Research 29:1133-1146.*
Bhattacharya et al. (2017, PLoS One 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101 (25):9205-10).*
Ulloa-Aguirre et al. (2004, Traffic 5:821-837).*
Bernier et al. (2004, Curr. Opin. Pharmacol. 4:528-533).*

(Continued)

*Primary Examiner* — Elizabeth C. Kemmerer
(74) *Attorney, Agent, or Firm* — Brian C Cholewa

(57) ABSTRACT

Compounds are provided herein for inducing weight loss and for treating diabetes, dyslipidemia, NASH and/or obesity. Also provided are pharmaceutical compositions containing such compounds and therapeutic uses of such compounds and compositions, where such compounds act as GDF15 agonists with extended time of action and other advantageous properties.

10 Claims, No Drawings

Specification includes a Sequence Listing.

(56) References Cited

OTHER PUBLICATIONS

Patent Cooperation Treaty International Search Report and the Written Opinion of the International Searching Authority pertaining to International Application No. PCT/US2019/024756; dated Jul. 5, 2019.

Xiong, Y., Walker, K., Min, X., Hale, C., Tran, T., Komorowski, R., . . . & Wang, X. (2017). Long-acting MIC-1/GDF15 molecules to treat obesity: Evidence from mice to monkeys. *Science translational medicine*, 9(412), eaan8732.

Johnen, H., Lin, S., Kuffner, T., Brown, D. A., Tsai, V. W. W., Bauskin, A. R., . . . & Hunter, M. (2007). Tumor-induced anorexia and weight loss are mediated by the TGF-β superfamily cytokine MIC-1. *Nature medicine*, 13(11), 1333.

Macia, L., Tsai, V. W. W., Nguyen, A. D., Johnen, H., Kuffner, T., Shi, Y. C., . . . & Sainsbury, A. (2012). Macrophage inhibitory cytokine 1 (MIC-1/GDF15) decreases food intake, body weight and improves glucose tolerance in mice on normal & obesogenic diets. *PloS one*, 7(4), e34868.

Tsai, V. W. W., Macia, L., Johnen, H., Kuffner, T., Manadhar, R., Jørgensen, S. B., . . . & Jiang, L. (2013). TGF-b superfamily cytokine MIC-1/GDF15 is a physiological appetite and body weight regulator. *PloS one*, 8(2), e55174.).

Cimino, I., Coll, A. P., & Yeo, G. S. (2017). GDF15 and energy balance: homing in on a mechanism. *Nature medicine*, 23(10), 1119.

Mullican, S. E., Lin-Schmidt, X., Chin, C. N., Chavez, J. A., Furman, J. L., Armstrong, A. A., . . . & Cavanaugh, C. R. (2017). GFRAL is the receptor for GDF15 and the ligand promotes weight loss in mice and nonhuman primates. *Nature medicine*, 23(10), 1150.

Yang, L., Chang, C. C., Sun, Z., Madsen, D., Zhu, H., Padkjær, S. B., . . . & Wang, J. (2017). GFRAL is the receptor for GDF15 and is required for the anti-obesity effects of the ligand. *Nature medicine*, 23(10), 1158.

Emmerson, P. J., Wang, F., Du, Y., Liu, Q., Pickard, R. T., Gonciarz, M. D., . . . & Foltz, L. A. (2017), The metabolic effects of GDF15 are mediated by the orphan receptor GFRAL. *Nature medicine*, 23(10), 1215.

Rose, R. J., Labrijn, A. F., van den Bremer, E. T., Loverix, S., Lasters, I., van Berkel P. H., . . . & Heck, A. J. (2011). Quantitative analysis of the interaction strength and dynamics of human IgG4 half molecules by native mass spectrometry. *Structure*, 19(9), 1274-1282.

Rose, R. J., van Berkel, P. H., van den Bremer, E. T., Labrijn, A. F., Vink, T., Schuurman, J., . . . & Parren, P. W. (Mar. 2013). Mutation of Y407 in the CH3 domain dramatically alters glycosylation and structure of human IgG. In *MAbs* (vol. 5, No. 2, pp. 219-228). Taylor & Francis.

* cited by examiner

GROWTH DIFFERENTIATION FACTOR 15 AGONIST COMPOUNDS AND METHODS OF USING THE SAME

The disclosure relates to biology and medicine, and more particularly, it relates to compounds and compositions including a growth differentiation factor 15 (GDF15) agonist compound having an extended time of action and other advantageous properties, as well as to methods of using the same for inducing weight loss and for treating diabetes, dyslipidemia, nonalcoholic steatohepatitis (NASH) and/or obesity.

GDF15 (also known as MIC-1, NAG-1) is a cysteine (Cys, C) knot protein belonging to the transforming growth factor-beta (TGFβ) superfamily. Its circulating concentration has been implicated in various biological functions, such as cancer cachexia and metabolism (see, Emmerson et al. (2017) *Nat. Med.* 23:1215-1219). Mature human GDF15 (SEQ ID NO:1) is a 112 amino acid peptide. Circulating GDF15 forms a homodimer of the mature protein (25 kDa) via what is reported to be one interchain disulfide bond between the Cys residue at position 77 of SEQ ID NO:1 on each chain of the homodimer (which corresponds to position 316 in SEQ ID NO:2). It is believed that homodimer formation is required for GDF15 biological activity (see, Intl. Patent Application Publication No. WO 2017/147742).

Among the many reported biological functions of a mature GDF15 homodimer, the regulation of energy homeostasis has gained attention due to its potential for treating obesity and type 2 diabetes (T2D). A connection between mature GDF15 homodimer activity and energy homeostasis is based on an observation that increasing serum levels of mature GDF15 correlate with weight loss in individuals with advanced prostate cancer (Emmerson et al. (2017)).

Moreover, increasing GDF15 in mice by administering recombinant GDF15 or through its expression and secretion from tumor xenografts illustrated that GDF15 induces weight loss via its ability to decrease food intake and increase energy expenditure. Furthermore, transgenic mice overexpressing GDF15 were resistant to diet-induced obesity and exhibited improved glucose tolerance, whereas GDF15 knockout mice had increased body weight and fat mass. GDF15-induced weight loss further was shown to reduce inflammatory responses and to increase lifespan in rodents.

Glial cell-derived neurotrophic factor (GDNF) receptor alpha-like (GFRAL) has been identified as the ligand binding receptor for GDF15. Loss of the anorectic effect of GDF15 in GFRAL-deficient mice as well as in rats administered an anti-GFRAL neutralizing monoclonal antibody illustrated that GFRAL is primarily responsible for the metabolic effects of GDF15 (Emmerson et al. (2017)).

The natural half-life ($t_{1/2}$) of mature circulating human GDF15 homodimer agonist is relatively short (about 2-3 hours). However, Intl. Patent Application Publication No. WO 2015/017710 generally describes extending the $t_{1/2}$ of GDF15 agonists through various conjugations including conjugation with a fragment crystallizable region (Fc).

The need exists for biologically active GDF15 compounds with extended time of action that may be used in therapy for inducing weight loss and for treating T2D, dyslipidemia, NASH and/or obesity. A therapeutically desirable compound would agonize the GFRAL receptor and provide advantageous properties. One advantageous property would be to induce weight loss. Another advantageous property would be stability in vivo for a prolonged window of time in the therapeutic range to enable a steady level of drug in the bloodstream with once weekly dosing to achieve the desired therapeutic effect. Further desirable properties also include decreased immunogenicity. Also, a desirable compound would have advantageous physical and/or chemical stability properties.

In view of the above, the disclosure describes biologically active GDF15 agonist compounds that have an extended $t_{1/2}$ and other desirable properties. More specifically, the compounds herein are recombinant fusion proteins having a hingeless monomeric (one Fc unit per GDF15) human IgG4 Fc linked via a rigid linker to the amino (N)-terminus of a GDF15 analog compound, whereby the compounds form a covalently linked homodimer via at least one interchain disulfide bond between the GDF15 portions of each of the monomers. An exemplary compound, Compound 2, is a homodimer of two molecules of Compound 1 (SEQ ID NO:2) and has surprisingly shown an enhanced $t_{1/2}$ of up to about 117 hours, which may provide for extended efficacy and may enable once weekly dosing of the compound. The compounds herein also have enhanced physical stability. For example, Compound 2 has a low 4.1% High Molecular Weight (HMW) soluble aggregate in Protein A capture pool. Compound 2 also exhibits enhanced chemical stability, such as a low 0.75% Low Molecular Weight (LMW) percent growth at 1 mg/ml after 4 weeks of storage at 40° C. in citrate at pH 6.0.

In one embodiment, a compound is provided that comprises SEQ ID NO:2.

In another embodiment, a compound is provided that includes a homodimer comprising two monomers, each including SEQ ID NO:2, wherein the two monomers are linked via at least one interchain disulfide bond between a Cys residue of the first monomer and a Cys residue of the second monomer.

In another embodiment, a pharmaceutical composition is provided that includes a compound having SEQ ID NO:2 or a homodimer of two monomers of SEQ ID NO:2 and one or more pharmaceutically acceptable excipients.

In another embodiment, a method is provided for inducing weight loss or for treating T2D, dyslipidemia, NASH and/or obesity in an individual that includes administering to the individual an effective amount of a compound having SEQ ID NO:2, a homodimer comprising two monomers of SEQ ID NO:2, or a pharmaceutical composition comprising the compound having SEQ ID NO:2 or the homodimer comprising two monomers of SEQ ID NO:2.

In another embodiment, a compound is provided that includes SEQ ID NO:2 or a homodimer comprising two monomers of SEQ ID NO:2 for use in therapy. Alternatively, a compound is provided that includes SEQ ID NO:2 or a homodimer comprising two monomers of SEQ ID NO:2 for use in inducing weight loss or for use in treating T2D, dyslipidemia, NASH and/or obesity.

In another embodiment, uses are provided for a compound including SEQ ID NO:2 or a homodimer comprising two monomers of SEQ ID NO:2 in the manufacture of a medicament for inducing weight loss or for treating T2D, dyslipidemia, NASH and/or obesity.

In other embodiments, a compound is provided that is produced by cultivating a mammalian cell including a cDNA molecule encoding a polypeptide comprising the amino acid sequence of SEQ ID NO:2, under such conditions that the polypeptide is expressed, and recovering the compound. Additionally, a method is provided for inducing weight loss in an individual or for treating T2D, dyslipidemia, NASH and/or obesity that includes administering to the individual an effective amount of a compound herein or a composition of herein once per week.

As used herein, "about" means within a statistically meaningful range of a value or values such as, for example, a stated concentration, length, molecular weight, pH, sequence identity, time frame, temperature, volume, etc. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, "effective amount" means an amount or dose of a compound herein or a pharmaceutical composition containing a compound herein, which upon single or multiple dose administration to the patient or subject, will elicit the biological or medical response of or desired therapeutic effect on a tissue, system, animal, mammal or human that is being sought by the researcher, veterinarian, medical doctor or other clinician. Preferably, an effective amount of a compound or compositions containing a compound of the present invention to a patient in need thereof would result in a net loss of body weight. A dose can include a higher initial loading dose, followed by a lower dose.

As used herein, "individual," "patient" and "subject" are used interchangeably and mean an animal, especially a human. When a human, the individual is characterized with a disease, disorder or condition that would benefit from administration of a compound or composition herein.

As used herein, "treatment" or "treating" means managing and caring for an individual having a condition for which GDF15 administration is indicated for the purpose of combating or alleviating symptoms and complications of those conditions. Treating includes administering a compound or composition including a compound herein to an individual in need thereof for preventing onset of symptoms or complications, alleviating symptoms or complications, or eliminating the disease, condition or disorder. In particular, treating includes administering a compound or composition including a compound herein to an individual in need thereof to result in a net loss of body weight. The individual being treated can be an animal, especially a human.

The pharmaceutical compositions herein may be administered parenterally to an individual in need of such treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump. Moreover, the pharmaceutical compositions can include one or more pharmaceutically acceptable excipients. Such pharmaceutical compositions may be prepared by any of a variety of techniques using conventional excipients for pharmaceutical products that are well known in the art (see, e.g., Remington's Pharmaceutical Sciences, 21st Edition, University of the Sciences in Philadelphia, Philadelphia, Pa., USA (2006)).

The compounds and compositions herein may be used in simultaneous, separate or sequential combination with one or more additional therapeutic agents useful for inducing weight loss and for treating diabetes, conditions related to T2D, dyslipidemia NASH and/or obesity. Non-limiting examples of the additional therapeutic agents that can be combined with the claimed compounds include, but are not limited to, insulin or insulin analogs; biguanides; sulfonylureas; thiazolidinediones; dipeptidyl peptidase-4 ("DPP-4") inhibitors; sodium-dependent glucose transporter (SGLT2) inhibitors; incretin compounds such as glucagon-like-peptide-1 (GLP-1) or GLP-1 analogs, gastric inhibitory polypeptide (GIP) or GIP analogs, oxyntomodulin (OXM) or OXM analogs; or combinations of any of the foregoing agents. The compounds herein and the additional therapeutic agent(s) can be administered either together through the same delivery route and device such as a single pill, capsule, tablet or injectable formulation; or separately administered either at the same time in separate delivery devices or routes; or administered sequentially.

The compounds herein may be prepared by a variety of techniques known to one of skill in the art. For example, the compounds may be prepared via production of a protein or precursor protein molecule using recombinant DNA techniques. The DNA, including cDNA and synthetic DNA, may be double-stranded or single-stranded. The coding sequences that encode the compounds may vary as a result of the redundancy or degeneracy of the genetic code. The DNA may be introduced into a host cell to produce the compound or precursor thereof. The host cells may be bacterial cells such as K12 or B strains of *Escherichia coli*, fungal cells such as yeast cells, or mammalian cells such as chinese hamster ovary ("CHO") cells.

An appropriate host cell is transiently or stably transfected or transformed with an expression system, such as expression vectors, for producing a compound here or a precursor thereof. Expression vectors typically are replicable in the host organisms either as episomes or as an integral part of the host chromosomal DNA. Commonly, expression vectors will contain selection markers such as, for example, tetracycline, neomycin, glutamine synthetase and dihydrofolate reductase, to permit selection of those cells transformed with the desired DNA sequences.

The compounds herein may be prepared by a variety of techniques known to one of skill in the art, as well as those methods described below. The specific biosynthetic or synthetic steps for each of the steps described may be used, not used or combined in different ways to prepare the compounds herein.

The GDF15 analog compounds herein can act as GFRAL compounds and are produced in a mammalian cell expression system using CHOK1 cell derivatives. Genes coding for the GDF15 proteins are sub-cloned into glutamine synthetase (GS)-containing expression plasmid backbones (pEE12.4-based plasmids). The cDNA sequence (SEQ ID NO:16) encoding Compound 1 (SEQ ID NO:2), an exemplary Fc-GDF15 protein, is fused in frame with the coding sequence of a signal peptide sequence, METDTLLL-WVLLLWVPGSTG (SEQ ID NO:3) to enhance secretion of the desired product into the tissue culture medium.

The expression is driven by the viral cytomegalovirus (CMV) promoter.

CHOK1 SV cells are stably transfected using electroporation and the appropriate amount of recombinant expression plasmid, and the transfected cells are maintained in suspension culture at an adequate cell density. Selection of the transfected cells is accomplished by growth in 25 μM methionine sulfoximine (MSX)-containing serum-free medium and incubated at about 35° C.-37° C. and about 5-7% $CO_2$. GDF15 proteins or Fc-GDF15 fusion proteins are secreted into the media from the CHO cells. The GDF15 portions of the proteins associate with one another, creating homodimers comprising two GDF15 proteins or Fc-GDF15 fusion protein homodimers connected to each other via an interchain disulfide bond. The GDF15 or Fc-GDF15 homodimers may be purified by Protein A affinity chromatography followed by anion exchange and hydrophobic chromatography.

GDF15 protein homodimers from harvested media are captured onto a Capto Blue resin (GE). Fc-GDF15 protein homodimers from harvested media are captured onto Mab Select Protein A resin (GE). The resin then is briefly washed with a running buffer, such as a phosphate-buffered saline (PBS; pH 7.4) or a running buffer containing Tris, to remove non-specifically bound material. The protein is eluted from the resin with a low pH solution, such as 10 mM citric acid pH 3. Fractions containing GDF15 proteins are pooled and may be held at a low pH to inactivate potential viruses. The pH can be neutralized by adding a base such as 0.1 M Tris pH 8.0. The GDF15 protein may be further purified by anion exchange chromatography using resins such as Poros XQ (Life Technologies). GDF15 protein is eluted from the AEX column using a 0 to 200 mM NaCl gradient in 50 mM Tris, pH 8.0 over 15 column volume.

The Fc-GDF15 fusion protein may be further purified by hydrophobic interaction chromatography by using a Capto Phenyl ImpRes Hydrophobic Interaction Chromatography (HIC) Column (GE Healthcare). The column is performed by adjusting the charge solution to around 0.5 M sodium sulfate and eluted using a 10 Column Volume (CV) gradient going from 0.5 M sodium sulfate in a 20 mM Tris pH 8 solution. After HIC, the protein may be further purified by size exclusion chromatography by loading the concentrated Capto Phenyl ImpRes pool on a Superdex200 (GE Healthcare) with isocratic elution in PBS pH 7.4.

Purified GDF15 compounds may be passed through a viral retention filter such as Planova 20N (Asahi Kasei Medical) followed by concentration/diafiltration into 10 mM citrate, 150 mM NaCl pH 7 using tangential flow ultrafiltration on a regenerated cellulose membrane (Millipore).

Soluble human GFRAL extracellular domain (ECD) is produced in a mammalian cell expression system using CHOK1 cell derivatives. Polyhistidine-tagged GFRAL ECD from harvested media is captured onto nickel-immobilized metal ion affinity chromatography (IMAC). The resin is then briefly washed with a running buffer, such as a PBS pH 7.4, or a running buffer containing Tris (pH 8.0, 500 mM NaCl) to remove non-specifically bound material. The bound HIS-tagged GFRAL ECD (SEQ ID NO:4) is eluted using 0-250 mM imidazole in PBS or TRIS, pH 8.0, 500 mM NaCl over 10 column volumes. The HIS-tagged GFRAL ECD may be further purified by size exclusion chromatography by loading concentrated IMAC pool on a Superdex200 (GE Healthcare) with isocratic elution in PBS (pH 7.4).

Mammalian expression of antibodies results in glycosylation. Typically, glycosylation occurs in the Fc region of an antibody at a highly conserved N-glycosylation site. N-glycans typically attach to asparagine. In a typical constant region of IgG immunoglobulins, there is only one site for N-linked glycosylation. This site can be modified, however, to prevent glycosylation or additional sites can be added for additional or diverse glycosylation structures. Also, glycosylation does occur occasionally in other regions of molecules expressed in mammalian cells.

The compounds herein are prepared in this manner or in a similar manner that would be readily determined by one of skill in the art.

EXAMPLES

The following non-limiting examples are offered for purposes of illustration, not limitation.

Example 1: In Vitro Receptor Affinity

In vitro binding parameters of the human GDF15 homodimer and exemplary Compound 2 to a human GFRAL receptor are determined by Surface Plasmon Resonance (SPR). The ECD of GFRAL includes three Cys-rich domains (D1, D2 and D3). The affinity of the homodimer of human GDF15 (des-ARN SEQ ID NO:1; that is, GDF15 lacking Ala, Arg and Asp from the N-terminal end) and Compound 2, a homodimer of the Fc-GDF15 Compound 1 (SEQ ID NO:2) to HIS-tagged human GFRAL ECD (SEQ ID NO:4) may be measured by SPR. The kinetics are summarized in Table 1.

To measure human GDF15 (des-ARN SEQ ID NO:1) or Compound 2 binding to human GFRAL ECD, a Biacore T200 Instrument is used to measure the binding kinetics of human GDF15 homodimer (des-ARN SEQ ID NO:1) and Compound 2 to the GFRAL ECD. Measurements are performed at 25° C. Samples are dissolved in HBS-EP+, pH 7.4 (GE Healthcare; 10 mM HEPES pH 7.4+150 mM NaCl+3 mM EDTA+0.05% surfactant P20). Goat anti-rabbit GDF15 antibody (R&D) is immobilized on the flow cells of a CM5 sensor chip using amine coupling chemistry. GDF15 samples are prepared at 25 µg/ml by dilution into running buffer.

Human GFRAL ECD samples are prepared at final concentrations of 1000, 500, 250, 125, 62.5, 31.3, 15.6, 7.8, 3.9, 2.0 and 0 (blank) nM by dilution into running buffer. The SPR experiment includes the following steps: (1) capturing GDF15 samples on separate flow cells (Fc2, Fc3 and Fc4), (2) injecting 200 µl of human GFRAL ECD over all flow cells at 100 l/min, (3) dissociating for 600 sec, (4) regenerating chip surfaces with a 10 µl (30 sec) injection of glycine, pH 1.5, at 20 l/min, and (5) equilibrating chip surfaces with a 10 µl (30 sec) injection of HBS-EP+ at 20 l/min. Each concentration of human GFRAL ECD is injected in duplicate.

Data are processed using standard double-referencing and fit to a 1:1 binding model using Biacore T200 Evaluation Software to determine the association rate ($k_{on}$, $M^{-1}s^{-1}$), dissociation rate ($k_{off}$, $s^{-1}$) and maximum response (Rmax; response units (RU)). The equilibrium dissociation constant ($K_D$) is calculated from the relationship $K_D = k_{off}/k_{on}$ (M).

TABLE 1

Binding Kinetics of Human GDF15 Homodimer and Compound 2 Homodimer to Human GFRAL ECD (D1-D2-D3-ECD) Receptor at 25° C.

| Compound | $k_{on}$ (1/Ms) | $k_{off}$ (1/s) | $K_D$ (nM) |
| --- | --- | --- | --- |
| Human GDF15 (homodimer of two compounds including des-ARN SEQ ID NO: 1) | 2.92E+05 | 7.21E−03 | 7.2 |
| Compound 2 (homodimer of two compounds including SEQ ID NO: 2) | 1.05E+06 | 8.71E−03 | 8.3 |

The results show that the human GDF15 homodimer (two compounds comprising des-ARN SEQ ID NO:1) had affinity of 7.2 nM for human GFRAL ECD, and the Compound 2 homodimer (two compounds comprising SEQ ID NO:2) had affinity of 8.3 nM for human GFRAL ECD.

Example 2: In Vitro Functional Activity

GFRAL, the receptor for GDF15, is a member of the GDNF receptor family and contains a single transmembrane domain and no intracellular signaling domain. Members of the GDNF receptor family including GFRAL utilize the co-receptor RET to transduce a signal. Stimulation of the GDNF receptor/RET complex is known to activate signal transduction networks involving ERK, AKT and STAT phosphorylation.

To assess the activity and relative potency of mature human GDF15 variants, HEK293 cells (ATCC) are transfected with CMV-driven mammalian expression vectors containing human GFRAL (NCBI Ref. Sequence No. NP_997293.2) and human RET51 (NCBI Ref. Sequence No. NP_066124.1) and grown for three weeks in the presence of geneticin and puromycin (Life Technologies) to create a pool of cells stably expressing both proteins. Measurement of ERK1/2 phosphorylation is chosen as an endpoint to assess RET activation utilizing an AlphaLISA Surefire Ultra Phospho-ERK1/2 Assay Kit (Perkin Elmer), according to the manufacturer's instructions, and an EnVision Multilabel Microplate Reader Model 2102 (Perkin Elmer).

Briefly, HEK293-hGFRAL/hRET cells, between Passage 10-20, are seeded at 20,000 cells per well on poly-D-lysine-coated 96-well plates and grown for three days at 37° C. in a 5% $CO_2$/95% $O_2$ atmosphere. Cells are incubated in serum-free media for 4 hrs and then treated, as indicated, for 10 min, lysed and frozen until assayed. Cell lysates are thawed by incubating for 1 hr at 4° C., mixed on an orbital plate shaker, and transferred to a white 384-well plate. The AlphaLISA "2-plates/i-incubation" method is utilized by adding Acceptor and Donor Mixes, supplied with the assay kit, to the lysates and incubating at room temperature in the dark for 8 hrs prior to measurement of AlphaLISA signal on the EnVision Plate Reader.

Each plate of cells used for an assay includes native human mature GDF15 as a reference standard for assay performance. ERK1/2 phosphorylation (pERK1/2) data from multiple plates are collected in a single graph by converting raw AlphaLISA signal data on the Y-axis to % Maxima relative to the human GDF15 reference standard utilizing the following formula:

% Maxima=100*(x−min)/(max−min), where min=0 and represents no stimulation, max=100 and represents the stimulation observed at a saturating dose of compound, and x=any given treatment. $EC_{50}$ for each compound is determined using a variable slope sigmoidal dose-response curve with four parameter logistic regression in GraphPad Prism version 7.00. The $EC_{50}$ listed for each compound in Table 2 is determined by generating the geometric mean of the $EC_{50}$ for 3 independent assays of each compound using the following formula:

Geomean=$\sqrt[3]{X1*X2*X3}$

HEK293 cells expressing both human GFRAL and human RET51 are used to assess the potency of Compound 2. Native human mature GDF15 (SEQ ID NO:1), as a homodimer, is used as a reference standard on each plate of cells. Test Articles are run in quadruplicate in three independent experiments.

Compound 2 Potency Comparison to Human GDF15.

| Test Article | $EC_{50}$ (pM) | SEM | N |
|---|---|---|---|
| Mature human GDF15 (homodimer of two compounds including SEQ ID NO: 1) | 27.9 | 2.9 | 3 |

-continued

Compound 2 Potency Comparison to Human GDF15.

| Test Article | $EC_{50}$ (pM) | SEM | N |
|---|---|---|---|
| Compound 2 (homodimer of two compounds including SEQ ID NO: 2) | 86.2 | 5.8 | 3 |

Data from a representative experiment are shown as mean ± SE
N, number of independent experiments Example 3: In Vivo Efficacy in Normal Rat Models Obesity is a common co-morbidity associated with diabetes and insulin resistance. GDF15 has been reported to suppress food intake, induce weight loss and improve glucose homeostasis. Therefore, a GDF15 compound may be effective in therapy for inducing weight loss and for conditions such as T2D, dyslipidemia, NASH and/or obesity. Compound 2 is administered in male Sprague Dawley rats for a period of 15 days with daily body weight and food intake measurements.

Normal male Sprague-Dawley rats (Envigo; 14 weeks old) are maintained on a regular chow diet upon arrival at the facility (TD2014; Teklad, Madison, Wis.) and are used in the following studies. Animals are individually housed in a temperature-controlled (24° C.) facility with 12-hour light/dark cycle (lights on 0600) and free access to food (TD2014) and water.

After a minimum of one week of acclimation to the facility, the rats are randomized according to their body weight, so that each experimental group of animals would have similar body weight. Body weights ranged from 332 to 369 grams.

All groups contain five rats. Vehicle or Compound 2 (dose range 0.01 to 0.3 mg/kg) dissolved in vehicle (PBS) are administered by subcutaneous (SC) injection (1 mL/kg) to ad libitum fed normal rats every 3 days for 15 days.

Subcutaneous injections are made on Day 1, 4, 7, 10 and 13. Daily body weight and food intake measurements are made throughout the study period. Percent body weight is calculated daily from each animal's initial body weight as follows:

% Body Weight=(Daily Body Weight/Initial Body Weight)×100.

All data are presented as the mean±SEM of five animals per group. The effective dose concentrations for percent weight loss and cumulative food intake are determined in GraphPad Prism using the non-linear fit tool. Statistical analysis is performed using repeated measures ANOVA, followed by Dunnett's method for multiple comparisons. Significant differences are identified at *−$p<0.05$, −$p<0.01$, *−$p<0.001$, ****−$p<0.0001$.

TABLE 3

Effect of Compound 2 Treatment on Percent Body Weight and Cumulative Food Intake in Normal SD Rats.

| Treatment | Body Weight (%) | Cumulative Food Intake (g) |
|---|---|---|
| Vehicle (1 ml/kg, SC) | 106.69 ± 0.54 | 264.48 ± 7.28 |
| Compound 2 (0.01 mg/kg) | 93.34 ± 2.13* | 193.04 ± 8.54* |
| Compound 2 (0.03 mg/kg) | 85.18 ± 2.60* | 155.42 ± 11.13* |
| Compound 2 (0.06 mg/kg) | 81.80 ± 1.66* | 122.54 ± 14.05* |

TABLE 3-continued

Effect of Compound 2 Treatment on Percent Body Weight and Cumulative Food Intake in Normal SD Rats.

| Treatment | Body Weight (%) | Cumulative Food Intake (g) |
|---|---|---|
| Compound 2 (0.1 mg/kg) | 78.30 ± 3.71* | 115.74 ± 15.75* |
| Compound 2 (0.3 mg/kg) | 73.57 ± 1.56* | 91.22 ± 8.57* |

All data are presented as the mean ± SEM of 5 animals per group from Day 14.
Statistical analysis was performed using repeated measures ANOVA, followed by Dunnett's method for multiple comparisons.
Significant differences were identified at *p < 0.05.

Chronic treatment with Compound 2 in normal SD male rats resulted in a statistically significant reduction in food intake and a statistically significant reduction in percent body weight at study completion compared to vehicle treated animals in a dose-dependent manner. The cumulative food intake is reduced from 264.48 to 91.22 at the highest dose tested and the body weight reduction ranges from a 7% to a 26% reduction. The data appear to indicate that Compound 2 has a statistically significant effect in reducing body weight and food intake in normal SD rats in a dose dependent manner.

Example 4: In Vivo Efficacy in Diet-Induced Obese (DIO) Mice

To investigate Compound 2's effect on weight loss, metabolism, body composition and hepatic steatosis, Compound 2 is chronically dosed to C57/Bl6 DIO mice.

Male C57/Bl6 DIO mice (Taconic) 24 to 25 weeks old, are maintained on a calorie rich diet upon arrival at the facility (TD95217; Teklad, Madison, Wis.) and are used in the following studies. Animals are individually housed in a temperature-controlled (24° C.) facility with 12-hour light/dark cycle (lights on 2200) and free access to food (TD95217) and water. After a minimum of 2 weeks acclimation to the facility, the mice are randomized according to their body weight, so that each experimental group of animals would have similar body weight. The body weights range from 40 to 50 grams.

All groups contain five mice. Vehicle or Compound 2 (0.002, 0.006, 0.02, 0.06, and 0.2 mg/kg) are dissolved in vehicle (PBS) and are administered by subcutaneous (SC) injection (10 mL/kg) to adlibitum-fed DIO mice 30 to 90 min prior to the onset of the dark cycle every 3 days for 21 days. SC injections are made on Day 1, 4, 7, 10, 13, 16, 19 and 22. Body weight and food intake are measured daily throughout the study.

Absolute changes in body weight are calculated by subtracting the body weight of the same animal prior to the first injection of molecule. On Day 17, animals are fasted at 0600 and at 1300, blood is collected to measure fasting blood glucose and insulin. Blood glucose is measured by AccuChek® Glucometers (Roche Diabetes Care, Inc.; Indianapolis, Ind.). Insulin is measured by ELISA (MSD, Rockville, Md.). Insulin resistance index is calculated by the formula:

$$\text{HOMA IR} = \text{fasting plasma insulin(mIUl/L)}*(\text{fasting blood glucose(mmol/L)})/22.5.$$

On Day 24, animals are sacrificed prior to the dark photoperiod, and the livers are removed and frozen. Liver triglycerides, determined from homogenates of livers collected at sacrifice, and plasma analytes are measured on the Hitachi Modular P Clinical Analyzer.

TABLE 4

Effect of Compound 2 Treatment on Body Weight and Cumulative Food Intake in DIO Mice on Day 16.

| Treatment | Body Weight Change From Initial Measurement (g) | Cumulative Food Intake (g) |
|---|---|---|
| Vehicle (10 ml/kg, SC) | −0.68 ± 0.14 | 41.30 ± 0.94 |
| Compound 2 (0.002 mg/kg) | −4.58 ± 0.71* | 33.22 ± 0.99* |
| Compound 2 (0.006 mg/kg) | −8.64 ± 0.41* | 29.24 ± 1.41* |
| Compound 2 (0.02 mg/kg) | −11.82 ± 0.57* | 23.00 ± 1.86* |
| Compound 2 (0.06 mg/kg) | −9.02 ± 0.57* | 23.86 ± 0.96* |
| Compound 2 (0.2 mg/kg) | −9.08 ± 0.59* | 27.52 ± 1.30* |

All data are presented as mean ± SEM of 5 animals per group.
Values are presented as mean ± SEM with n = 5.
*p < 0.05 compared to vehicle group; one-way ANOVA, followed by Dunnett's method for multiple comparisons.

TABLE 5

Effect of Compound 2 Treatment on Serum Glucose, Cholesterol, Alanine Aminotransferase (ALT) and Liver Triglycerides in DIO Mice on Day 24.

| Treatment | Glucose (mg/dL) | Cholesterol (mg/dL) | ALT (IU/L) | Liver Triglycerides (mg/g tissue) |
|---|---|---|---|---|
| Vehicle (10 ml/kg, SC) | 339.18 ± 30.58 | 271.80 ± 12.02 | 310.80 ± 34.92 | 210.10 ± 11.82 |
| Compound 2 (0.002 mg/kg) | 317.52 ± 17.95 | 220.80 ± 4.89* | 231.60 ± 25.39 | 69.88 ± 18.88* |
| Compound 2 (0.006 mg/kg) | 261.00 ± 20.43* | 177.00 ± 7.82* | 159.60 ± 73.32* | 46.56 ± 13.85* |
| Compound 2 (0.02 mg/kg) | 223.38 ± 16.02* | 172.80 ± 18.51* | 87.00 ± 13.04* | 24.82 ± 8.80* |
| Compound 2 (0.06 mg/kg) | 245.94 ± 10.10* | 199.20 ± 15.34* | 114.60 ± 22.72* | 58.90 ± 14.45* |
| Compound 2 (0.2 mg/kg) | 241.02 ± 8.88* | 167.40 ± 8.72* | 112.80 ± 19.15* | 34.62 ± 10.88* |

Values are presented as mean ± SEM with n = 5.
*p < 0.05 compared to vehicle group; one-way ANOVA, followed by Dunnett's.

TABLE 6

Effect of Compound 2 Treatment on Fasting Blood Glucose, Insulin and HOMA-IR in DIO Mice on Day 17.

| Treatment | Fasting Glucose (mmol/L) | Fasting Insulin (mIU/L/mL) | HOMA-IR |
|---|---|---|---|
| Vehicle (10 ml/kg, SC) | 6.80 ± 0.28 | 85.64 ± 13.68 | 25.78 ± 4.13 |
| Compound 2 (0.002 mg/kg) | 6.64 ± 0.28 | 45.94 ± 4.66* | 13.51 ± 1.32* |
| Compound 2 (0.06 mg/kg) | 5.16 ± 0.53* | 26.44 ± 2.95* | 6.22 ± 1.15* |

All data were presented as mean ± SEM of 5 animals per group from Day 17.
Statistical analysis was performed using repeated measures ANOVA, followed by Dunnett's method for multiple comparisons.
Significant differences were identified at $p < 0.05$.

Compound 2 dose-dependently reduces body weight and food intake in male DIO mice, which indicates it could be used in therapy for inducing weight loss and for obesity (Table 4). Compound 2 also reduces serum glucose, which indicates it could be used in therapy for diabetes (Table 5). Compound 2 further reduces cholesterol, which indicates it could be used in therapy for dyslipidemia (Table 5). Compound 2 improves liver health (demonstrated by decrease of serum ALT) and reduces liver triglycerides, which indicates it could be used in therapy for NASH (Table 5). Fasting blood glucose and insulin testing done on Day 17 demonstrates increased insulin sensitivity and a reduced insulin resistance index, which further support the possibility of using Compound 2 in therapy for diabetes (Table 6).

Example 5: Stability of Different Fc-GDF15 Constructs

Protein aggregation in a pharmaceutical product is not desired because it lowers overall production yield, and it could trigger an immune response when administered to individuals. Thus, maintaining the compound in the monomeric state, or in this case a covalently bound homodimer, is preferred.

To test the propensity of different GDF15 fusion proteins to aggregate and/or degrade, various Fc-GDF15 fusion proteins may be expressed in mammalian CHO cells. Fc-GDF15 fusion proteins may be captured onto Mab Select Protein A (GE; Piscataway, N.J.) with PBS (pH 7.4) running buffer; briefly may be washed with running buffer to remove non-specifically bound material; and may be eluted with 20 mM acetic acid and 5 mM citric acid, pH 3. Fractions containing Fc-GDF15 proteins are pooled, and pH is neutralized by adding 1/10 volume of 1 M Tris pH 8.0.

Protein A capture pool is then analyzed by size exclusion chromatography (SEC) to determine the % High Molecular Weight aggregate (HMW), indicating how much aggregation had occurred. The SEC separation method is performed on a Tosoh Bioscience 3000SWXL, 5 μm Column with dimensions 30 cm×0.78 cm. Mobile phase is PBS×1, 350 mM NaCl (pH 7.4) at a flow rate of 0.5 mL/min. Initial low concentration samples are applied as 10 mcL injections and monitored at an absorbance wavelength of 214 nm. The % LMW species indicates chemical stability, or small molecular weight degradation products of a compound.

TABLE 7

Comparison of Physical and Chemical Stability of Different Fc-GDF15 Fusion Proteins.

| Compound | % HMW | % LMW |
|---|---|---|
| Compound 2 (including monomeric Fc) | 4.1 | 2.3 |
| Compound 3 (including tandem Fc) | 60.8 | 3.6 |
| Compound 4 (including heterodimeric Fc) | 2.0 | 49.1 |

A tandem Fc-GDF15 fusion protein construct (two similar Fc portions of antibody is attached to one another end-to-end, containing a hinge region, and then is attached to a GDF15 molecule where the GDF15 portions then self-associate to create a dimer), Compound 3 (homodimer of two molecules, each comprising SEQ ID NO:5) has a 60.8% HMW compared to the 4.1% HMW of Compound 2. This suggests that Compound 2 has better physical stability, with lower aggregation and less risk of immunogenic aggregates than a tandem Fc-GDF15 fusion protein construct.

A heterodimeric Fc-GDF15 (two different Fc portions of an antibody that associate with one another side-by-side and where one Fc portion (Chain B, SEQ ID NO:17) is associated with another Fc portion which is attached to a GDF15 molecule (Chain A, SEQ ID NO:6) and where the GDF15 portions then self-associate to create a homodimer), Compound 4 (a homodimer of two molecules, each molecule comprising a heterodimer of SEQ ID NO:6 & SEQ ID NO:17) has a high 49.1% LMW species compared to Compound 2, which has only 2.3% LMW, suggesting that Compound 2 has better chemical stability and decreased propensity to chemical or proteolytic cleavages. Chemical stability and avoiding degradation helps to retain the potency of a compound over long periods of time. Also, less degradation minimizes the risk that degradation byproducts will cause further potency problems by interfering with the active ingredient in a formulation or that degradation byproducts will aggregate and cause immunogenicity issues.

Example 6: Stability of Double Versus Single Fc Mutations

The unique structure of the Fc portion of the compounds herein, with two specific mutations, unexpectedly exhibits better stability and higher solubility at high concentrations than an Fc construct with either one of the mutations alone. Two Fcs with a single mutation are generated to disrupt the CH3/CH3 association in the IgG4-Fc and to create a monomeric Fc construct. The first was Compound 7, with a glutamine substituted for a phenylalanine at position 405 in a full length human IgG4 heavy chain, corresponding to position 173 in SEQ ID NO:2 (position 175 in SEQ ID NO:9). The second single mutant generated was Compound 8, an Fc with a glutamic acid substituted for a tyrosine at position 407 in a full length human IgG4 heavy chain, corresponding to position 175 in SEQ ID NO:2 (position 177 in SEQ ID NO:10). A dual Fc mutant, Compound 5 (SEQ ID NO:7), also is generated, and it contains both the Fc mutations from Compounds 7 and 8. Compound 5 is the same sequence as Compound 2 except an additional two amino acids, AP, are present at the N-terminus of the Fc region in Compound 5. Compounds 2, 5, 7 and 8 are lacking the hinge region of ESKYGPPCPPCP (SEQ ID NO:8) to ensure formation of the monomeric IgG4 Fc.

The compounds in this example are expressed in mammalian CHO cells, and the harvested media is captured onto Mab Select Protein A (GE) with PBS (pH 7.4) running buffer; briefly washed with running buffer to remove non-specifically bound material; and eluted with 20 mM acetic acid and 5 mM citric acid, pH 3.0. Fractions containing GDF15 proteins are pooled and pH is neutralized by adding 1/10 volume of 1 M Tris pH 8.0.

Neutralized protein A capture pools are then buffer exchanged in 10 mM citrate pH 5.0 in Amicon Ultra 0.5 ml Centrifugal Concentrator with 10 MWCO. The single and double Fc-GDF15 mutants are next attempted to concentrate up to or above 10 mg/ml by using Amicon Ultra 0.5 ml Centrifugal Concentrator with 10 MWCO.

TABLE 8

Maximum Solubility of GDF15 Fusions at pH 5.0.

| Compound | Max solubility at pH 5.0 (mg/ml) | Visual observations |
|---|---|---|
| Homodimer of Compound 7 (SEQ ID NO: 9) | 1.7 | Unable to achieve 10 mg/ml; observed precipitation during concentration |
| Homodimer of Compound 8 (SEQ ID NO: 10) | 6.7 | Unable to achieve 10 mg/ml, observed precipitation during concentration |
| Homodimer of Compound 5 (SEQ ID NO: 7) | 9.8 | Clear solution |
| Monomeric IgG4 Fc-only control | 12.0 | Clear solution |

The results show that single Fc mutants, the homodimers of Compound 7 and Compound 8, had reduced solubility when compared to the double Fc mutant, the homodimer of Compound 5. The homodimer of Compound 7 could not achieve 10 mg/ml due to precipitation and material loss. The homodimer of Compound 8 showed improved solubility when compared to the homodimer of Compound 7; however, it was not able to achieve 10 mg/ml due to material loss during the concentration process. The homodimer of Compound 5, with the novel double mutation in the Fc, retained solubility at 9.8 mg/ml. A monomeric IgG4 Fc only control was soluble up to 12 mg/ml.

Example 7: Comparison of Chemical Stability for Flexible or Rigid Linkers

To test the chemical stability of GDF15 compounds herein, such compounds may be dialyzed overnight at 4° C. into the following buffers: 10 mM citrate, pH6 (C6), 10 mM citrate, pH7 (C7), 10 mM Tris, pH 7.0 (T7), 10 mM Tris, pH 8.0 (T8) or 1×PBS, pH 7.4 (PBS). To assess long-term stability of Fc-GDF15 fusions 1.0 mg/mL protein solutions in respective buffers may be stored at 4° C., 25° C. and 40° C. for 4 weeks, and the % LMW is determined by analytical SEC.

The SEC separation method may be performed on a Tosoh Bioscience 3000SWXL, 5 μm Column with dimensions 30 cm×0.78 cm. Mobile phase may be PBS, 350 mM NaCl, pH 7.4 at a flow rate of 0.5 mL/min. Initial low concentration samples may be applied as 10 mcL injections and monitored at an absorbance wavelength of 214 nm.

Changes in chemical stability, measured by % LMW, are evaluated relative to the time 0 samples. As determined by studies conducted essentially as described above, the % LMW growth for GDF15 compounds are summarized in Table 9.

The compounds tested are Compound 2, a homodimer of Compound 1 (SEQ ID NO:2), with a rigid G4-AP10-G4 linker, a homodimer of Compound 5 (SEQ ID NO:7) with a flexible L5Q linker (GGGGQGGGGQGGGGQGGGGQGGGGQ (SEQ ID NO: 12)), and a homodimer of Compound 6 (SEQ ID NO: 11), with a rigid G4S-AP10-G4S linker.

TABLE 9

Growth in % LMW for GDF15 Compounds at 1 mg/ml as Determined by Analytical SEC.

| | % LMW Growth at 1 mg/ml after 4 weeks of storage at 4° C., 25° C. and 40° C. | | | | | | | | |
|---|---|---|---|---|---|---|---|---|---|
| | Citrate pH 6.0 | | | Citrate pH 7.0 or Tris pH 7.0 | | | Tris pH 8.0 or PBS pH 7.4 | | |
| | 4° C. | 25° C. | 40° C. | 4° C. | 25° C. | 40° C. | 4° C. | 25° C. | 40° C. |
| Compound 2 Linker: GGGG-AP10-GGGG | 0 | 0 | 0.75 | 0 | 0.36 | 3.45 | 0.15 | 0.99 | 7.09 |
| Homodimer of Compound 5 Linker: L5Q | 0.37 | 0.81 | 3.99 | 0.56 | 1.8 | 6.63 | 0.71 | 2.8 | 10.5 |
| Homodimer of Compound 6 Linker: GGGGS-AP10-GGGGS | 1.65 | 0.76 | 2.7 | 1.52 | 1.2 | 5.76 | 1.83 | 1.52 | 5.65 |

The L5Q linker has a higher % LMW after storage at 25° C. and 40° C. than either of the AP10 linkers, suggesting a higher propensity to chemical degradation for GDF15 fusion proteins comprising an L5Q flexible linker than a protein comprising an AP10 (APAPAPAPAPAPAPAPAPAP; SEQ ID NO:13) rigid linker. Also, the homodimer of Compound 6, with a linker comprising G4S (GGGGS; SEQ ID NO: 14), has a higher % LMW than Compound 2, with a linker comprising G4 (GGGG; SEQ ID NO:15), in most conditions, suggesting greater chemical stability of Compound 2 with its G4-AP10-G4 linker.

The chemical and physical stability of the GDF15 compounds with rigid (Compound 2 and Compound 6) and flexible linkers (Compound 5) may be assessed at high concentration of 10 mg/ml. Compounds may be first dialyzed O/N at 4° C. into following buffers: (a) 10 mM citrate pH 6.5; (b) 10 mM citrate pH 6.5, 150 mM NaCl; and (c) 10 mM citrate pH 6.5, 0.02% Polysorbate 80. Excipients such as 150 mM NaCl and 0.02% Polysorbate are added to the formulation to test their effect on chemical and physical stability of the GDF15 fusions. Next, compounds may be concentrated to 10 mg/ml using 10,000 MWCO, 15 ml Millipore Spin Concentrators. After concentration, the % HMW and % LMW may be determined by SEC using the concentrated protein (t=0).

The SEC separation method may be performed on a Tosoh Bioscience 3000SWXL, 5 μm Column with dimensions 30 cm×0.78 cm. Mobile phase was PBS, 350 mM NaCl, pH 7.4 at a flow rate of 0.5 mL/min. 10 mg/ml samples are diluted to 1 mg/ml in their respective buffers and then are applied as 10 mcL injections and monitored at an absorbance wavelength of 214 nm.

The 10 mg/ml formulations may be incubated for 4 weeks at 4° C., 25° C. and 40° C. to assess longer-term stability under stress conditions. The % LMW and % HMW may be determined again at 4 weeks time (t=4w) by SEC. Changes in chemical stability (% LMW) may be evaluated relative to the time 0 samples.

TABLE 10

Chemical Stability Represented as Growth in % LMW for GDF15 Compounds at 10 mg/ml.

| | % LMW Growth at 10 mg/ml after 4 weeks of storage at 4° C., 25° C. and 40° C. | | | | | | | | |
|---|---|---|---|---|---|---|---|---|---|
| | Citrate pH 6.5 | | | Citrate pH 6.5 + 150 mM NaCl | | | Citrate pH 6.5 + 0.02% Polysorbate 80 | | |
| | 4° C. | 25° C. | 40° C. | 4° C. | 25° C. | 40° C. | 4° C. | 25° C. | 40° C. |
| Homodimer of Compound 5 Linker: L5Q | 0.52 | 1.03 | 6.39 | 0.25 | 0.86 | 5.11 | 0.27 | 1.04 | 6.2 |
| Homodimer of Compound 6 Linker: GGGGS-AP10-GGGGS | 0 | 0.2 | 2.73 | 0 | 0.3 | 2.52 | 0 | 0.31 | 2.8 |

TABLE 11

Physical Stability Represented as Growth in % HMW for GDF15 Compounds at 10 mg/ml.

| | % HMW Growth at 10 mg/ml after 4 weeks of storage at 4, 25 and 40° C. | | | | | | | | |
|---|---|---|---|---|---|---|---|---|---|
| | Citrate pH 6.5 | | | Citrate pH 6.5 + 150 mM NaCl | | | Citrate pH 6.5 + 0.02% Polysorbate 80 | | |
| | 4° C. | 25° C. | 40° C. | 4° C. | 25° C. | 40° C. | 4° C. | 25° C. | 40° C. |
| Homodimer of Compound 5 Linker: L5Q | 0.06 | 0.23 | 3.04 | 0.05 | 0.19 | 7.3 | 0.1 | 0.24 | 3.13 |
| Homodimer of Compound 6 Linker: GGGGS-AP10-GGGGS | 0 | 0.1 | 2.98 | 0 | 0.33 | 7.18 | 0 | 0 | 2.85 |

As shown in Table 10, the homodimer of Compound 5 at 10 mg/ml, containing a flexible linker, showed a higher level of % LMW than the homodimer of Compound 6, with a rigid linker, at 25° C. and 40° C., which indicates lower chemical stability.

As shown in Table 11, the homodimer of Compound 5 at 10 mg/ml, containing a flexible linker, showed a higher level of % HMW than the homodimer of Compound 6, with a rigid linker, which indicates lower physical stability. Low chemical and/or physical stability can cause precipitation and possible immunogenicity issues.

Example 8: Pharmacokinetic Behavior of GDF15 Compounds

The pharmacokinetic behavior of Compound 2 is tested in monkeys. Plasma concentrations of GDF15 compounds are determined by an ELISA method at Eli Lilly and Company (Indianapolis, Ind.). The sandwich ELISA uses a polyclonal goat anti-human GDF15 (R&D Systems/AF957) or monoclonal mouse anti-human/primate GDF15 antibody (R&D Systems/MAB957) coated at 1 or 3 μg/mL as the capture reagent. The GDF15 compound then is detected with either a mouse anti-human IgG4 pFc-HRP antibody (Southern Biotech/9190-05) or a mouse anti-human IgG Fc-HRP antibody (Southern Biotech/9200-05). The plates are developed using the tetramethylbenzidine (TMB) substrate system (SeraCare/5120), and the enzymatic reaction is quenched with TMB Stop Solution (KPL/50-85-04).

Male Cynomolgus monkeys are administered a single subcutaneous dose (0.3 mg/kg) of Compound 2 in PBS (pH 7.4) at a volume of 0.5 mL/kg. Blood is collected from each animal at pre-dose and at 6, 24, 48, 72, 96, 168, 240, 336, 408 and 504 hrs post-dose for pharmacokinetic characterization.

TABLE 12

Individual and Mean Pharmacokinetic Parameters Following a Single 0.3 mg/kg Subcutaneous Dose to Male Cynomolgus Monkeys.

| Compound (Dose) | Animal | $t_{1/2}$ (hr) | $T_{max}$ (hr) | $C_{max}$ (μg/mL) | $AUC_{0\text{-}inf}$ (hr*μg/mL) | CL/F (mL/hr/kg) |
|---|---|---|---|---|---|---|
| Compound 2 (0.3 mg/kg) | 1 | 118 | 48 | 1.96 | 206 | 1.45 |
|  | 2 | 116 | 48 | 2.44 | 184 | 1.63 |
|  | Mean | 117 | 48 | 2.20 | 195 | 1.54 |

Abbreviations:
$AUC_{0\text{-}inf}$ = area under the curve from time 0 hours to infinity,
CL/F = clearance/bioavailability,
$T_{max}$ = time to maximal concentration,
$C_{max}$ = maximum observed plasma concentration,
$t_{1/2}$ = half-life.

The data in Table 12 show that the $t_{1/2}$ in monkeys is measured at 117 hrs. This is an unexpectedly long $t_{1/2}$ for a monomeric Fc molecule. Also, the pharmacokinetic profile in monkeys is stable for a prolonged window of time, which suggests that the pharmacokinetic profile of Compound 2 in humans also could be demonstrably stable for a prolonged window of time in the therapeutic range to enable a steady level of drug in the bloodstream with once weekly dosing.

SEQUENCES

The following nucleic and/or amino acid sequences are referred to in this disclosure and are provided below for reference.

SEQ ID NO: 1
Mature human GDF15
ARNGDHCPLGPGRCCRLHTVRASLEDLGWADWVLSPREVQVTMCIGACPS
QFRAANMHAQIKTSLHRLKPDTVPAPCCVPASYNPMVLIQKTDTGVSLQT
YDDLLAKDCHCI SEQ ID NO: 2
Fusion protein
EAAGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWE
SNGQPENNYKTTPPVLDSDGSFQLESRLTVDKSRWQEGNVFSCSVMHEAL
HNHYTQKSLSLSLGGGGGAPAPAPAPAPAPAPAPAPAPGGGGGDHCPLGP
GRCCRLHTVRASLEDLGWADWVLSPREVQVTMCIGACPSQFRAANMHAQI
KTSLHRLKPDTVPAPCCVPASYNPMVLIQKTDTGVSLQTYDDLLAKDCHC
I SEQ ID NO: 3
Leader sequence
METDTLLLWVLLLWVPGSTG SEQ ID NO: 4
Artificial sequence
QTNNCTYLREQCLRDANGCKHAWRVMEDACNDSDPGDPCKMRNSSYCNLS
IQYLVESNFQFKECLCTDDFYCTVNKLLGKKCINKSDNVKEDKFKWNLTT
RSHEGFKGMWSCLEVAEACVGDVVCNAQLASYLKACSANGNPCDLKQCQA
AIRFFYQNIPFNIAQMLAFCDCAQSDIPCQQSKEALHSKTCAVNMVPPPT
CLSVIRSCQNDELCRRHYRTFQSKCWQRVTRKCHEDENCISTLSKQDLTC
SGSDDCKAAYIDILGTVLQVQCTCRTITQSEESLCKIFQHMLHRKSCFNY
PTLSNVKGMALYTRKHANKHHHHHH SEQ ID NO: 5
Artificial sequence
ERKSSVECPPCPAPPVAGPSVFLFPPKPKDTLMISRTPEVTCVVVDVSHE
DPEVQFNWYVDGVEVHNAKTKPREEQFNSTERVVSVLTVVHQDWLNGKEY
KCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQQ
GNVFSCSVMHEALHNHYTQKSLSLSPGGGGGSGGGGSGGGGSGGGGSGGG
GSGGGGSGGGGSGGGSERKSSVECPPCPAPPVAGPSVFLFPPKPKDTLM
ISRTPEVTCVVVDVSHEDPEVQFNWYVDGVEVHNAKTKPREEQFNSTFRV
VSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDG
SFFLYSKLTVDKSRWQQGNVFSCSVMHEALHNHYTQKSLSLSPGGGGSGG
GGASARNGDHCPLGPGRCCRLHTVRASLEDLGWADWVLSPREVQVTMCIG
ACPSQFRAANMHAQIKTSLHRLKPDTVPAPCCVPASYNPMVLIQKTDTGV
SLQTYDDLLAKDCHCI SEQ ID NO: 6
Artificial sequence
DKTHTCPPCPAPALGGPSVFLFPPKPKDTLMISRTPEVTCVVVDVSHEDP
EVKFNWYVDGVEVHNAKTKPREEQYNSTYRVVSVLTVLHQDWLNGKEYKC
KVSNKALPAPIEKTISKAKGQPREPQVYTLPPSREEMTKNQVSLWCLVKG -continued
FYPSDIAVEWESNGQPENNYKTTPPVLDSDGSFFLYSKLTVDKSRWQQGN
VFSCSVMHEALHNHYTQKSLSLSPGKGGGGSGGGGSGGGGSGGGGSGGGG
SNGTHCPLGPGRCCRLHTVRASLEDLGWADWVLSPREVQVTMCIGACPSQ
FRAANMHAQIKTSLHRLKPDTVPAPCCVPASYNPMVLIQKTDTGVSLQTY
DDLLAKDCHCI SEQ ID NO: 7
Artificial sequence
APEAAGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFQLESRLTVDKSRWQEGNVFSCSVMHE
ALHNHYTQKSLSLSLGGGGGQGGGGQGGGGQGGGGQGGGGQGGGGDHCPL
GPGRCCRLHTVRASLEDLGWADWVLSPREVQVTMCIGACPSQFRAANMHA
QIKTSLHRLKPDTVPAPCCVPASYNPMVLIQKTDTGVSLQTYDDLLAKDC
HCI SEQ ID NO: 8
Fc fragment
ESKYGPPCPPCP SEQ ID NO: 9
Artificial sequence
APEAAGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFQLYSRLTVDKSRWQEGNVESCSVMHE
ALHNHYTQKSLSLSLGGGGGQGGGGQGGGGQGGGGQGGGGQGGGGDHCPL
GPGRCCRLHTVRASLEDLGWADWVLSPREVQVTMCIGACPSQFRAANMHA
QIKTSLHRLKPDTVPAPCCVPASYNPMVLIQKTDTGVSLQTYDDLLAKDC
HCI SEQ ID NO: 10
Artificial sequence
APEAAGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFFLESRLTVDKSRWQEGNVFSCSVMHE
ALHNHYTQKSLSLSLGGGGGQGGGGQGGGGQGGGGQGGGGQGGGGDHCPL
GPGRCCRLHTVRASLEDLGWADWVLSPREVQVTMCIGACPSQFRAANMHA
QIKTSLHRLKPDTVPAPCCVPASYNPMVLIQKTDTGVSLQTYDDLLAKDC
HCI SEQ ID NO: 11
Artificial sequence
APEAAGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVE
WESNGQPENNYKTTPPVLDSDGSFQLESRLTVDKSRWQEGNVFSCSVMHE
ALHNHYTQKSLSLSLGGGGGSAPAPAPAPAPAPAPAPAPAPGGGGSDHC
PLGPGRCCRLHTVRASLEDLGWADWVLSPREVQVTMCIGACPSQFRAANM
HAQIKTSLHRLKPDTVPAPCCVPASYNPMVLIQKTDTGVSLQTYDDLLAK
DCHCI SEQ ID NO: 12
Artificial sequence
GGGGQGGGGQGGGGQGGGGQGGGGQ SEQ ID NO: 13
Artificial sequence
APAPAPAPAPAPAPAPAPAP SEQ ID NO: 14
Artificial sequence
GGGGS SEQ ID NO: 15
Artificial sequence
GGGG SEQ ID NO: 16
Artificial sequence
gaggccgccggggggaccatcagtcttcctgttccccccaaaacccaagga
cactctcatgatctcccggacccctgaggtcacgtgcgtggtggtggacg
tgagccaggaagaccccgaggtccagttcaactggtacgtggatggcgtg
gaggtgcataatgccaagacaaagccgcgggaggagcagttcaacagcac
gtaccgtgtggtcagcgtcctcaccgtcctgcaccaggactggctgaacg
gcaaggagtacaagtgcaaggtctccaacaaaggcctcccgtcctccatc
gagaaaaccatctccaaagccaaagggcagccccgagagccacaggtgta
caccctgcccccatcccaggaggagatgaccaagaaccaggtcagcctga
cctgcctggtcaaaggcttctaccccagcgacatcgccgtggagtgggaa
agcaatgggcagccggagaacaactacaagaccacgcctcccgtgctgga
ctccgacggctccttcgcactcgagagcaggctaaccgtggacaagagca
ggtggcaggaggggaatgtcttctcatgctccgtgatgcatgaggctctg
cacaaccactacacacagaagagcctctccctgtctctgggtggcggtgg
tggagctccagccccagctcctgctcctgcaccagcacctgccccgctc
cagcacccgcacctggaggaggggcggtgaccactgtccctggggcct
ggccggtgttgcagactgcatacagtccgggcctccctggaagacctggg
ttgggcagattgggtgctctcacctcgcgaggttcaggtgaccatgtgca
ttggggcttgtccctcacaatttcgcgcagctaacatgcacgcccaaatc
aaaacctccctgcaccggcttaaaccggatactgttcctgctccctgctg
cgtgccagcatcctacaaccccatggtgctgatccagaagacggatacag
gggtgtcactgcagacctatgatgacctcctggccaaagattgccactgt
atc SEQ ID NO: 17
Artificial sequence
DKTHTCPPCPAPALAGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLSCAVK
GFYPSDIAVEWESNGQPENNYKTTPPVLDSDGSFFLVSKLTVDKSRWQQG
NVFSCSVMHEALHNHYTQKSLSLSPGK

The invention claimed is:

1. A compound comprising the amino acid sequence set forth in SEQ ID NO:2.

2. A compound consisting of the amino acid sequence set forth in SEQ ID NO:2.

3. A homodimer comprising two compounds of claim 1, wherein the compounds are linked via at least one interchain disulfide bond between a cysteine residue of the first compound and a cysteine residue of the second compound.

4. A pharmaceutical composition comprising the compound of claim 1 and one or more pharmaceutically acceptable excipients.

5. A method of inducing weight loss in an individual, the method comprising the step of:
administering to the individual an effective amount of the compound of claim 1 or the composition of claim 4.

6. A method of treating type 2 diabetes in an individual, the method comprising the step of:
administering to the individual an effective amount of the compound of claim 1 or the composition of claim 4.

7. A method of treating obesity in an individual, the method comprising the step of:
administering to the individual an effective amount of the compound of claim 1 or the composition of claim 4.

8. A method of treating nonalcoholic steatohepatitis (NASH) in an individual, the methods comprising the step of:
administering to the individual an effective amount of the compound of claim 1 or the composition of claim 4.

9. A method of treating dyslipidemia in an individual, the method comprising the step of:
administering to the individual an effective amount of the compound of claim 1 or the composition of claim 4.

10. A compound produced by cultivating a mammalian cell comprising a cDNA molecule encoding a polypeptide comprising the amino acid sequence set forth in SEQ ID NO:2 under such conditions that the polypeptide is expressed, and recovering the compound.

* * * * *

SEQUENCE LISTING

<160> NUMBER OF SEQ ID NOS: 17

<210> SEQ ID NO 1
<211> LENGTH: 112
<212> TYPE: PRT
<213> ORGANISM: Homo sapiens

<400> SEQUENCE: 1

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 2
<211> LENGTH: 351
<212> TYPE: PRT
<213> ORGANISM: Artificial Sequence
<220> FEATURE:
<223> OTHER INFORMATION: Synthetic Construct

<400> SEQUENCE: 2

```
Glu Ala Ala Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Gln Leu Glu Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205
```

```
Leu Ser Leu Ser Leu Gly Gly Gly Gly Ala Pro Ala Pro
        210                 215                 220
Ala Pro Ala Pro Ala Pro Ala Pro Ala Pro Ala Pro Gly Gly
225                 230                 235                 240
Gly Gly Gly Asp His Cys Pro Leu Gly Pro Gly Arg Cys Cys Arg Leu
                245                 250                 255
His Thr Val Arg Ala Ser Leu Glu Asp Leu Gly Trp Ala Asp Trp Val
                260                 265                 270
Leu Ser Pro Arg Glu Val Gln Val Thr Met Cys Ile Gly Ala Cys Pro
        275                 280                 285
Ser Gln Phe Arg Ala Ala Asn Met His Ala Gln Ile Lys Thr Ser Leu
        290                 295                 300
His Arg Leu Lys Pro Asp Thr Val Pro Ala Pro Cys Cys Val Pro Ala
305                 310                 315                 320
Ser Tyr Asn Pro Met Val Leu Ile Gln Lys Thr Asp Thr Gly Val Ser
                325                 330                 335
Leu Gln Thr Tyr Asp Asp Leu Leu Ala Lys Asp Cys His Cys Ile
                340                 345                 350

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Met Glu Thr Asp Thr Leu Leu Leu Trp Val Leu Leu Leu Trp Val Pro
1               5                   10                  15
Gly Ser Thr Gly
            20

<210> SEQ ID NO 4
<211> LENGTH: 325
<212> TYPE: PRT
<213> ORGANISM: Artificial Sequence
<220> FEATURE:
<223> OTHER INFORMATION: Synthetic Construct

<400> SEQUENCE: 4

Gln Thr Asn Asn Cys Thr Tyr Leu Arg Glu Gln Cys Leu Arg Asp Ala
1               5                   10                  15
Asn Gly Cys Lys His Ala Trp Arg Val Met Glu Asp Ala Cys Asn Asp
            20                  25                  30
Ser Asp Pro Gly Asp Pro Cys Lys Met Arg Asn Ser Ser Tyr Cys Asn
        35                  40                  45
Leu Ser Ile Gln Tyr Leu Val Glu Ser Asn Phe Gln Phe Lys Glu Cys
    50                  55                  60
Leu Cys Thr Asp Asp Phe Tyr Cys Thr Val Asn Lys Leu Leu Gly Lys
65                  70                  75                  80
Lys Cys Ile Asn Lys Ser Asp Asn Val Lys Glu Asp Lys Phe Lys Trp
                85                  90                  95
Asn Leu Thr Thr Arg Ser His His Gly Phe Lys Gly Met Trp Ser Cys
            100                 105                 110
Leu Glu Val Ala Glu Ala Cys Val Gly Asp Val Val Cys Asn Ala Gln
        115                 120                 125
Leu Ala Ser Tyr Leu Lys Ala Cys Ser Ala Asn Gly Asn Pro Cys Asp
```

```
                130                 135                 140
Leu Lys Gln Cys Gln Ala Ala Ile Arg Phe Phe Tyr Gln Asn Ile Pro
145                 150                 155                 160

Phe Asn Ile Ala Gln Met Leu Ala Phe Cys Asp Cys Ala Gln Ser Asp
                165                 170                 175

Ile Pro Cys Gln Gln Ser Lys Glu Ala Leu His Ser Lys Thr Cys Ala
            180                 185                 190

Val Asn Met Val Pro Pro Thr Cys Leu Ser Val Ile Arg Ser Cys
        195                 200                 205

Gln Asn Asp Glu Leu Cys Arg Arg His Tyr Arg Thr Phe Gln Ser Lys
    210                 215                 220

Cys Trp Gln Arg Val Thr Arg Lys Cys His Glu Asp Glu Asn Cys Ile
225                 230                 235                 240

Ser Thr Leu Ser Lys Gln Asp Leu Thr Cys Ser Gly Ser Asp Asp Cys
                245                 250                 255

Lys Ala Ala Tyr Ile Asp Ile Leu Gly Thr Val Leu Gln Val Gln Cys
                260                 265                 270

Thr Cys Arg Thr Ile Thr Gln Ser Glu Glu Ser Leu Cys Lys Ile Phe
            275                 280                 285

Gln His Met Leu His Arg Lys Ser Cys Phe Asn Tyr Pro Thr Leu Ser
        290                 295                 300

Asn Val Lys Gly Met Ala Leu Tyr Thr Arg Lys His Ala Asn Lys His
305                 310                 315                 320

His His His His His
                325

<210> SEQ ID NO 5
<211> LENGTH: 616
<212> TYPE: PRT
<213> ORGANISM: Artificial Sequence
<220> FEATURE:
<223> OTHER INFORMATION: Synthetic Construct

<400> SEQUENCE: 5

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
```

```
                165                 170                 175
Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Gly Gly Gly Ser Gly Gly Gly Ser Gly Gly Gly
225                 230                 235                 240

Gly Ser Gly Gly Gly Ser Gly Gly Gly Ser Gly Gly Gly
            245                 250                 255

Ser Gly Gly Gly Ser Gly Gly Gly Ser Glu Arg Lys Ser Ser
            260                 265                 270

Val Glu Cys Pro Pro Cys Pro Ala Pro Val Ala Gly Pro Ser Val
            275                 280                 285

Phe Leu Phe Pro Pro Lys Pro Lys Asp Thr Leu Met Ile Ser Arg Thr
            290                 295                 300

Pro Glu Val Thr Cys Val Val Asp Val Ser His Glu Asp Pro Glu
305                 310                 315                 320

Val Gln Phe Asn Trp Tyr Val Asp Gly Val Glu Val His Asn Ala Lys
            325                 330                 335

Thr Lys Pro Arg Glu Glu Gln Phe Asn Ser Thr Phe Arg Val Val Ser
            340                 345                 350

Val Leu Thr Val Val His Gln Asp Trp Leu Asn Gly Lys Glu Tyr Lys
            355                 360                 365

Cys Lys Val Ser Asn Lys Gly Leu Pro Ala Pro Ile Glu Lys Thr Ile
            370                 375                 380

Ser Lys Thr Lys Gly Gln Pro Arg Glu Pro Gln Val Tyr Thr Leu Pro
385                 390                 395                 400

Pro Ser Arg Glu Glu Met Thr Lys Asn Gln Val Ser Leu Thr Cys Leu
            405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Met Leu Asp Ser
            435                 440                 445

Asp Gly Ser Phe Phe Leu Tyr Ser Lys Leu Thr Val Asp Lys Ser Arg
            450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Gly Gly
            485                 490                 495

Gly Ser Gly Gly Gly Gly Ala Ser Ala Arg Asn Gly Asp His Cys Pro
            500                 505                 510

Leu Gly Pro Gly Arg Cys Cys Arg Leu His Thr Val Arg Ala Ser Leu
            515                 520                 525

Glu Asp Leu Gly Trp Ala Asp Trp Val Leu Ser Pro Arg Glu Val Gln
            530                 535                 540

Val Thr Met Cys Ile Gly Ala Cys Pro Ser Gln Phe Arg Ala Ala Asn
545                 550                 555                 560

Met His Ala Gln Ile Lys Thr Ser Leu His Arg Leu Lys Pro Asp Thr
            565                 570                 575

Val Pro Ala Pro Cys Cys Val Pro Ala Ser Tyr Asn Pro Met Val Leu
            580                 585                 590
```

-continued

Ile Gln Lys Thr Asp Thr Gly Val Ser Leu Gln Thr Tyr Asp Asp Leu
            595                 600                 605

Leu Ala Lys Asp Cys His Cys Ile
        610                 615

<210> SEQ ID NO 6
<211> LENGTH: 361
<212> TYPE: PRT
<213> ORGANISM: Artificial Sequence
<220> FEATURE:
<223> OTHER INFORMATION: Synthetic Construct

<400> SEQUENCE: 6

Asp Lys Thr His Thr Cys Pro Pro Cys Pro Ala Pro Ala Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Trp Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys Gly Gly Gly Gly Ser Gly Gly Gly Gly Ser Gly Gly Gly Gly
225                 230                 235                 240

Ser Gly Gly Gly Gly Ser Gly Gly Gly Gly Ser Asn Gly Thr His Cys
                245                 250                 255

Pro Leu Gly Pro Gly Arg Cys Cys Arg Leu His Thr Val Arg Ala Ser
            260                 265                 270

Leu Glu Asp Leu Gly Trp Ala Asp Trp Val Leu Ser Pro Arg Glu Val
        275                 280                 285

Gln Val Thr Met Cys Ile Gly Ala Cys Pro Ser Gln Phe Arg Ala Ala
    290                 295                 300

Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
                325                 330                 335

Leu Ile Gln Lys Thr Asp Thr Gly Val Ser Leu Gln Thr Tyr Asp Asp
                340                 345                 350

Leu Leu Ala Lys Asp Cys His Cys Ile
            355                 360

<210> SEQ ID NO 7
<211> LENGTH: 353
<212> TYPE: PRT
<213> ORGANISM: Artificial Sequence
<220> FEATURE:
<223> OTHER INFORMATION: Synthetic Construct

<400> SEQUENCE: 7

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
                180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Gln Gly Gly
        210                 215                 220

Gly Gln Gly Gly Gly Gly Gln Gly Gly Gly Gln Gly Gly Gly Gly
225                 230                 235                 240

Gln Gly Gly Gly Gly Asp His Cys Pro Leu Gly Pro Gly Arg Cys Cys
                245                 250                 255

Arg Leu His Thr Val Arg Ala Ser Leu Glu Asp Leu Gly Trp Ala Asp
                260                 265                 270

Trp Val Leu Ser Pro Arg Glu Val Gln Val Thr Met Cys Ile Gly Ala
            275                 280                 285

Cys Pro Ser Gln Phe Arg Ala Ala Asn Met His Ala Gln Ile Lys Thr
        290                 295                 300

Ser Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

```
Val Ser Leu Gln Thr Tyr Asp Asp Leu Leu Ala Lys Asp Cys His Cys
            340                 345                 350

Ile

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Glu Ser Lys Tyr Gly Pro Pro Cys Pro Pro Cys Pro
1               5                   10

<210> SEQ ID NO 9
<211> LENGTH: 353
<212> TYPE: PRT
<213> ORGANISM: Artificial Sequence
<220> FEATURE:
<223> OTHER INFORMATION: Synthetic Construct

<400> SEQUENCE: 9

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Gly Gly Gly Gln Gly Gly Gly
    210                 215                 220

Gly Gln Gly Gly Gly Gly Gln Gly Gly Gly Gly Gln Gly Gly Gly Gly
225                 230                 235                 240

Gln Gly Gly Gly Gly Asp His Cys Pro Leu Gly Pro Gly Arg Cys Cys
                245                 250                 255

Arg Leu His Thr Val Arg Ala Ser Leu Glu Asp Leu Gly Trp Ala Asp
            260                 265                 270
```

```
Trp Val Leu Ser Pro Arg Glu Val Gln Val Thr Met Cys Ile Gly Ala
            275                 280                 285
Cys Pro Ser Gln Phe Arg Ala Ala Asn Met His Ala Gln Ile Lys Thr
290                 295                 300
Ser Leu His Arg Leu Lys Pro Asp Thr Val Pro Ala Pro Cys Cys Val
305                 310                 315                 320
Pro Ala Ser Tyr Asn Pro Met Val Leu Ile Gln Lys Thr Asp Thr Gly
                325                 330                 335
Val Ser Leu Gln Thr Tyr Asp Asp Leu Leu Ala Lys Asp Cys His Cys
            340                 345                 350
Ile
```

<210> SEQ ID NO 10
<211> LENGTH: 353
<212> TYPE: PRT
<213> ORGANISM: Artificial Sequence
<220> FEATURE:
<223> OTHER INFORMATION: Synthetic Construct

<400> SEQUENCE: 10

```
Ala Pro Glu Ala Ala Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser Gln Glu Asp Pro Glu Val Gln Phe Asn Trp Tyr
        35                  40                  45
Val Asp Gly Val Glu Val His Asn Ala Lys Thr Lys Pro Arg Glu Glu
50                  55                  60
Gln Phe Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Gly Leu Pro Ser Ser Ile Glu Lys Thr Ile Ser Lys Ala Lys Gly Gln
            100                 105                 110
Pro Arg Glu Pro Gln Val Tyr Thr Leu Pro Pro Ser Gln Glu Glu Met
        115                 120                 125
Thr Lys Asn Gln Val Ser Leu Thr Cys Leu Val Lys Gly Phe Tyr Pro
130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Glu Ser Arg Leu Thr Val Asp Lys Ser Arg Trp Gln Glu Gly Asn Val
            180                 185                 190
Phe Ser Cys Ser Val Met His Glu Ala Leu His Asn His Tyr Thr Gln
        195                 200                 205
Lys Ser Leu Ser Leu Ser Leu Gly Gly Gly Gly Gln Gly Gly Gly Gly
210                 215                 220
Gly Gln Gly Gly Gly Gly Gln Gly Gly Gly Gly Gln Gly Gly Gly Gly
225                 230                 235                 240
Gln Gly Gly Gly Gly Asp His Cys Pro Leu Gly Pro Gly Arg Cys Cys
                245                 250                 255
Arg Leu His Thr Val Arg Ala Ser Leu Glu Asp Leu Gly Trp Ala Asp
            260                 265                 270
```

```
Trp Val Leu Ser Pro Arg Glu Val Gln Val Thr Met Cys Ile Gly Ala
            275                 280                 285

Cys Pro Ser Gln Phe Arg Ala Ala Asn Met His Ala Gln Ile Lys Thr
        290                 295                 300

Ser Leu His Arg Leu Lys Pro Asp Thr Val Pro Ala Pro Cys Cys Val
305                 310                 315                 320

Pro Ala Ser Tyr Asn Pro Met Val Leu Ile Gln Lys Thr Asp Thr Gly
                325                 330                 335

Val Ser Leu Gln Thr Tyr Asp Asp Leu Leu Ala Lys Asp Cys His Cys
            340                 345                 350

Ile

<210> SEQ ID NO 11
<211> LENGTH: 355
<212> TYPE: PRT
<213> ORGANISM: Artificial Sequence
<220> FEATURE:
<223> OTHER INFORMATION: Synthetic Construct

<400> SEQUENCE: 11

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Gly Gly Gly Ser Ala Pro Ala
210                 215                 220

Pro Ala Pro Ala Pro Ala Pro Ala Pro Ala Pro Ala Pro Ala Pro Ala
225                 230                 235                 240

Pro Gly Gly Gly Gly Ser Gly Asp His Cys Pro Leu Gly Pro Gly Arg
                245                 250                 255

Cys Cys Arg Leu His Thr Val Arg Ala Ser Leu Glu Asp Leu Gly Trp
            260                 265                 270

Ala Asp Trp Val Leu Ser Pro Arg Glu Val Gln Val Thr Met Cys Ile
```

```
                    275                 280                 285

Gly Ala Cys Pro Ser Gln Phe Arg Ala Ala Asn Met His Ala Gln Ile
    290                 295                 300

Lys Thr Ser Leu His Arg Leu Lys Pro Asp Thr Val Pro Ala Pro Cys
305                 310                 315                 320

Cys Val Pro Ala Ser Tyr Asn Pro Met Val Leu Ile Gln Lys Thr Asp
                325                 330                 335

Thr Gly Val Ser Leu Gln Thr Tyr Asp Asp Leu Leu Ala Lys Asp Cys
            340                 345                 350

His Cys Ile
        355

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Gly Gly Gly Gly Gln Gly Gly Gly Gln Gly Gly Gly Gln Gly
1               5                   10                  15

Gly Gly Gly Gln Gly Gly Gly Gly Gln
            20                  25

<210> SEQ ID NO 13
<211> LENGTH: 20
<212> TYPE: PRT
<213> ORGANISM: Artificial Sequence
<220> FEATURE:
<223> OTHER INFORMATION: Synthetic Construct

<400> SEQUENCE: 13

Ala Pro Ala Pro Ala Pro Ala Pro Ala Pro Ala Pro Ala Pro Ala Pro
1               5                   10                  15

Ala Pro Ala Pro
            20

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gly
1

<210> SEQ ID NO 16
<211> LENGTH: 1053
<212> TYPE: DNA
```

<213> ORGANISM: Artificial Sequence
<220> FEATURE:
<223> OTHER INFORMATION: Synthetic Construct

<400> SEQUENCE: 16

```
gaggccgccg ggggaccatc agtcttcctg ttcccccaa aacccaagga cactctcatg      60
atctcccgga cccctgaggt cacgtgcgtg gtggtggacg tgagccagga agaccccgag     120
gtccagttca actggtacgt ggatggcgtg gaggtgcata atgccaagac aaagccgcgg     180
gaggagcagt tcaacagcac gtaccgtgtg gtcagcgtcc tcaccgtcct gcaccaggac     240
tggctgaacg gcaaggagta caagtgcaag gtctccaaca aaggcctccc gtcctccatc     300
gagaaaacca tctccaaagc caaagggcag ccccgagagc cacaggtgta caccctgccc     360
ccatcccagg aggagatgac caagaaccag gtcagcctga cctgcctggt caaaggcttc     420
taccccagcg acatcgccgt ggagtgggaa agcaatgggc agccggagaa caactacaag     480
accacgcctc ccgtgctgga ctccgacggc tccttccagc tcgagagcag gctaaccgtg     540
gacaagagca ggtggcagga ggggaatgtc ttctcatgct ccgtgatgca tgaggctctg     600
cacaaccact acacacagaa gagcctctcc ctgtctctgg gtggcggtgg tggagctcca     660
gccccagctc ctgctcctgc accagcacct gcccccgctc agcacccgc  acctggagga    720
ggggcggtg accactgtcc cctggggcct ggccggtgtt gcagactgca tacagtccgg     780
gcctccctgg aagacctggg ttgggcagat tgggtgctct cacctcgcga ggttcaggtg     840
accatgtgca ttgggcttg tccctcacaa tttcgcgcag ctaacatgca cgcccaaatc     900
aaaacctccc tgcaccggct taaaccggat actgttcctg ctccctgctg cgtgccagca     960
tcctacaacc ccatggtgct gatccagaag acggatacag gggtgtcact gcagacctat    1020
gatgacctcc tggccaaaga ttgccactgt atc                                 1053
```

<210> SEQ ID NO 17
<211> LENGTH: 227
<212> TYPE: PRT
<213> ORGANISM: Artificial Sequence
<220> FEATURE:
<223> OTHER INFORMATION: Synthetic Construct

<400> SEQUENCE: 17

```
Asp Lys Thr His Thr Cys Pro Pro Cys Pro Ala Pro Ala Leu Ala Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                 70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140
```

-continued

```
Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```